US012383191B1

(12) United States Patent
Taylor-Weiner et al.

(10) Patent No.: US 12,383,191 B1
(45) Date of Patent: Aug. 12, 2025

(54) SYSTEMS AND METHODS FOR ASSESSING LIVER PATHOLOGY

(71) Applicant: PathAI, Inc., Boston, MA (US)

(72) Inventors: Amaro N. Taylor-Weiner, Brooklyn, NY (US); Harsha Vardhan Pokkalla, Sudbury, MA (US); Hunter L. Elliott, Boston, MA (US); Benjamin P. Glass, Boston, MA (US); Ilan N. Wapinski, Brookline, MA (US); Aditya Khosla, Lexington, MA (US); Murray Resnick, Sharon, MA (US); Michael C. Montalto, Brielle, NJ (US); Andrew H. Beck, Brookline, MA (US); Zahil Shanis, Claymont, DE (US); Aryan Pedawi, Austin, TX (US); Quang Huy Le, Malden, MA (US); Jason K. Wang, Los Angeles, CA (US); Maryam Pouryahya, Bethesda, MD (US); Kenneth Knute Leidal, Cambridge, MA (US); Oscar M. Carrasco-Zevallos, Somerville, MA (US); Dinkar Juyal, Boston, MA (US); Charles Biddle-Snead, New York, NY (US); Katy Wack, Pittsburgh, PA (US)

(73) Assignee: PathAI, Inc., Boston, MA (US)

( * ) Notice: Subject to any disclaimer, the term of this patent is extended or adjusted under 35 U.S.C. 154(b) by 934 days.

(21) Appl. No.: 17/306,155

(22) Filed: May 3, 2021

Related U.S. Application Data

(60) Provisional application No. 63/157,224, filed on Mar. 5, 2021, provisional application No. 63/019,836, filed on May 4, 2020.

(51) Int. Cl.
*A61B 5/00* (2006.01)
*G06T 7/00* (2017.01)
(Continued)

(52) U.S. Cl.
CPC .......... *A61B 5/4244* (2013.01); *A61B 5/7267* (2013.01); *G06T 7/0012* (2013.01);
(Continued)

(58) Field of Classification Search
CPC ... A61B 5/4244; A61B 5/7267; G06T 7/0012; G06T 2207/20081; G06T 2207/20084;
(Continued)

(56) References Cited

U.S. PATENT DOCUMENTS

2018/0099001 A1\* 4/2018 Schentag ............ G01N 33/6893
2018/0140219 A1\* 5/2018 Yin ...................... A61B 5/0816
(Continued)

OTHER PUBLICATIONS

[No Author Listed], Gilead Announces Topline Results From Phase 2 ATLAS Study in Patients With Bridging Fibrosis (F3) and Compensated Cirrhosis (F4) Due to Nonalcoholic Steatohepatitis (NASH). Gilead Sciences, Inc. Dec. 16, 2019; 2 pages.
(Continued)

*Primary Examiner* — Jacky X Zheng
(74) *Attorney, Agent, or Firm* — Wolf, Greenfield & Sacks, P.C.

(57) ABSTRACT

In some aspects, the described systems and methods provide for a method for training a deep learning model to assess liver pathology, including accessing annotated liver pathology images associated with a group of patients in one or more randomized controlled clinical trials of nonalcoholic steatohepatitis therapy, each of the annotated liver pathology images including at least one annotation describing one or more tissue characteristic categories for a portion of the image, and training the deep learning model based on the annotated liver pathology images to predict the tissue characteristic categories, selected from a group comprising steatosis, lobular inflammation, hepatocyte ballooning, and fibrosis stage.

11 Claims, 5 Drawing Sheets

(51) Int. Cl.
*G16H 50/30* (2018.01)
*G16H 70/60* (2018.01)

(52) U.S. Cl.
CPC ............. *G16H 50/30* (2018.01); *G16H 70/60* (2018.01); *G06T 2207/20081* (2013.01); *G06T 2207/20084* (2013.01); *G06T 2207/30056* (2013.01)

(58) Field of Classification Search
CPC .......... G06T 2207/30056; G16H 50/30; G16H 70/60
USPC ......................................................... 382/128
See application file for complete search history.

(56) References Cited

U.S. PATENT DOCUMENTS

| | | | | |
|---|---|---|---|---|
| 2018/0256526 | A1* | 9/2018 | Hu | A61K 31/045 |
| 2019/0019300 | A1* | 1/2019 | Simpson | G06T 7/40 |
| 2019/0021677 | A1* | 1/2019 | Grbic | G06T 7/11 |
| 2020/0085382 | A1* | 3/2020 | Taerum | G06T 7/0016 |
| 2022/0076410 | A1* | 3/2022 | Georgescu | G06T 7/0012 |
| 2022/0245802 | A1* | 8/2022 | Wang | G16H 50/20 |

OTHER PUBLICATIONS

[No Author Listed], Noncirrhotic Nonalcoholic Steatohepatitis With Liver Fibrosis: Developing Drugs for Treatment. U.S. Department of Health and Human Services. Food and Drug Administration Center for Drug Evaluation and Research (CDER). Dec. 2018; 12 pages.

Ajmera et al., Refining Sample-Size Estimations Based Upon Placebo Response in Trials of Agents for Nonalcoholic Fatty Liver Disease. Clinical Gastroenterology and Hepatology. 2019; 17(4): 607-609.

Brener, Transient Elastography for Assessment of Liver Fibrosis and Steatosis: An Evidence-Based Analysis. Ontario Health Technology Assessment Series. Nov. 2015; 15(18):1-45.

Estes et al., Modeling the Epidemic of Nonalcoholic Fatty Liver Disease Demonstrates an Exponential Increase in Burden of Disease. Hepatology. 2018; 67(1): 123-133.

Forlano et al. High-Throughput, Machine Learning-Based Quantification of Steatosis, Inflammation, Ballooning, and Fibrosis in Biopsies From Patients With Nonalcoholic Fatty Liver Disease. Clinical Gastroenterology Hepatology. 2020; 18(9):2081-2090.

Frohmader et al., 1-Wasserstein Distance on the Standard Simplex. AStat Algebraic Statistics. 2021; 12(1):43-56.

Goodman, Grading and staging systems for inflammation and fibrosis in chronic liver diseases. Journal of Hepatology. 2007: 47; 598-607.

Han et al., Rates of and Factors Associated With Placebo Response in Trials of Pharmacotherapies for Nonalcoholic Steatohepatitis: Systematic Review and Meta-analysis. Clinical Gastroenterology and Hepatology. Mar. 2019; 17: 616-629.e26.

Harrison et al. Selonsertib for Patients with Bridging Fibrosis or Compensated Cirrhosis Due to NASH: Results from Randomized Ph III Stellar Trials. Journal of Hepatology. 2020; 73:26-39.

Juluri et al., Generalizability of the Nonalcoholic Steatohepatitis Clinical Research Network Histologic Scoring System for Nonalcoholic Fatty Liver Disease. J. Clin. Gastroenterol. Jan. 2011; 45(1): 55-58.

Kleiner et al., Design and Validation of a Histological Scoring System for Nonalcoholic Fatty Liver Disease. Hepatology. Jun. 2005; 41(6):1313-1321.

Levina et al., The Earth Mover's Distance is the Mallows Distance: Some Insights from Statistics. Proc. IEEE Int. Conf. Comput. Vis. 2001; 2:251-256.

Lichtinghagen et al., The Enhanced Liver Fibrosis (ELF) score: Normal values, influence factors and proposed cut-off values. Journal of Hepatology. 2013; 59: 236-242.

Loomba et al., Placebo in Nonalcoholic Steatohepatitis: Insight Into Natural History and Implications for Future Clinical Trials. Clin. Gastroenterol. Hepatol. Nov. 2008; 6(11): 1243-1248.

Merriman et al., Correlation of Paired Liver Biopsies in Morbidly Obese Patients With Suspected Nonalcoholic Fatty Liver Disease. Hepatology. 2006; 44(4): 874-880.

Olkin et al. The Distance between Two Random Vectors with Given Dispersion Matrices. Linear Algebra and Its Applications. 1982; 48:257-263.

Panaretos et al., Statistical Aspects of Wasserstein Distances. Annu. Rev. Stat. Its Appl. 6. 2019; 405-431.

Poole et al., Combining dependent P-values with an empirical adaptation of Brown's method. Bioinformatics. 2016; 32: i430-i436.

Storey et al., Statistical significance for genomewide studies. Proc. Natl. Acad. Sci. U. S. A. Aug. 5, 2003; 100(16): 9440-9445.

Vanderbeck et al., Automatic classification of white regions in liver biopsies by supervised machine learning. Human Pathology. 2014; 45:785-792.

Vanderbeck et al., Automatic quantification of lobular inflammation and hepatocyte ballooning in nonalcoholic fatty liver disease liver biopsies. Human Pathology. 2015; 46:767-775.

Younossi et al., Nonalcoholic Steatohepatitis Is the Fastest Growing Cause of Hepatocellular Carcinoma in Liver Transplant Candidates. Clinical Gastroenterology and Hepatology. 2019; 17: 748-755.e3.

* cited by examiner

SYSTEMS AND METHODS FOR ASSESSING LIVER PATHOLOGY

CROSS REFERENCE TO RELATED APPLICATIONS

This application claims priority under 35 U.S.C. § 119 (e) to U.S. Provisional Application Ser. No. 63/019,836, titled "SYSTEMS AND METHODS FOR ASSESSING LIVER PATHOLOGY," filed May 4, 2020 and U.S. Provisional Application Ser. No. 63/157,224, titled "SYSTEMS AND METHODS FOR ASSESSING LIVER PATHOLOGY," filed Mar. 5, 2021, each of which is hereby incorporated herein by reference in its entirety.

BACKGROUND

The prevalence of nonalcoholic fatty liver disease (NAFLD) is rising rapidly worldwide. NAFLD represents a continuum of disease with milder forms consisting of simple steatosis, while the progressive form, nonalcoholic steatohepatitis (NASH), can progress to cirrhosis and liver decompensation. NASH-related cirrhosis today represents the fastest growing indication for liver transplantation in the United States.

The accurate and reproducible assessment of NASH histology by a pathologist is considered to be the standard for making a diagnosis of NASH and informs clinical decision-making related to prognosis. This diagnosis is based on a scoring system derived from the Nonalcoholic Steatohepatitis Clinical Research Network (NASH CRN), and consists of a composite ordinal scoring system, the NAFLD Activity Score (NAS), comprising steatosis, lobular inflammation, and hepatocyte ballooning.

SUMMARY

The inventors have appreciated that a drawback of an ordinal scoring approach, such as the NAS and CRN fibrosis scoring systems, is that ordinal classification systems are unsuitable for a disease process that represents a continuum of severity of cellular and stromal injury. The inventors have also recognized that the degree of inter- and intra-observer variability between expert liver pathologists further supports this drawback of the NAS and CRN fibrosis scoring systems, which rely on manual review by a pathologist. The inventors have appreciated that a further problem with the NAS and CRN fibrosis scoring systems is the high rate of "histological response" observed in placebo treated patients which creates major challenges for adequately powering clinical trials of NASH therapeutics using histological endpoints. However, the current regulatory framework for approval of NASH therapeutics continues to rely on manual histological scoring, despite its significant limitations.

The inventors have recognized that there is a critical need for improved tools for the assessment of liver pathology to stratify risk and monitor treatment response in NASH. Accordingly, the inventors have developed a machine learning (ML)-based approach to liver pathology to characterize disease severity and monitor treatment response in NASH. For example, using samples from randomized controlled trials in NASH, the inventors have built and validated ML models to measure the core components of the NAFLD activity score and stage liver fibrosis by the CRN and/or ISHAK systems. While the CRN system uses a 0 to 4 stage scale for assessing fibrosis, the ISHAK system uses a 0-6 stage scale. The described systems and methods however are not limited to the CRN and ISHAK systems and may be equally applicable to other suitable measurement systems. The inventors have found that ML-generated data shows strong correlation with pathologist data and can be more predictive of disease progression and clinical events than manual scoring. The ML-based approach can outperform manual pathologic scoring for the prediction of disease progression and assessment of therapeutic response in NASH and demonstrates the power of machine learning to advance understanding of disease heterogeneity and drive the development of effective therapies for NASH.

In some aspects, the described systems and methods provide for training a deep learning model to assess liver pathology, including accessing annotated liver pathology images associated with a group of patients in one or more randomized controlled clinical trials of nonalcoholic steatohepatitis therapy, each of the annotated liver pathology images including at least one annotation describing one or more tissue characteristic categories for a portion of the image, and training the deep learning model based on the annotated liver pathology images to predict the tissue characteristic categories, selected from a group comprising steatosis, lobular inflammation, hepatocyte ballooning, and fibrosis stage.

In some embodiments, the method further comprises measuring a feature at or prior to the therapy of a patient, and measuring the same feature at a time point following therapy of the same patient and calculating differences in feature values to determine treatment-dependent effects.

In some embodiments, the method further comprises processing, using the trained deep learning model, a liver pathology image to generate predicted one or more tissue characteristic categories for the liver pathology image and generating, for the liver pathology image, based on the predicted one or more tissue characteristic categories, a slide-level continuous score that corresponds to an underlying heterogeneous pattern of fibrosis observed in the liver pathology image. In some embodiments, the one or more tissue characteristic categories are predicted on a pixel-level basis. In some embodiments, the slide-level continuous score represents a continuum of severity of cellular and stromal injury to capture disease heterogeneity among different patients, wherein an ordinal classification system does not capture the disease heterogeneity among the different patients.

In some embodiments, a group comprising steatosis, lobular inflammation, and hepatocyte ballooning corresponds to components of a nonalcoholic fatty liver disease activity score (NAS). In some embodiments, the method further comprises, for a liver pathology image, evaluating a performance of the deep learning model by comparing a fraction of tissue area in the liver pathology image assigned to each NAS component with an ordinal score determined by a pathologist, wherein the ordinal score is determined based on the NAS components. In some embodiments, intra-observer reproducibility of the ordinal score of the liver pathology image by multiple pathologists is lower than reproducibility of predictions from multiple iterations of the trained deep learning model processing the liver pathology image.

In some embodiments, the method further comprises extracting values for complex features from each of the annotated liver pathology images, including one or more features not included in the NAS components and training the deep learning model based on the annotated liver pathology images and the values for the complex features. In some embodiments, the complex features comprise at least one ratio of the NAS components, including a ratio of area of hepatocellular ballooning to steatosis. In some embodiments, the one or more features not included in the NAS components include portal inflammation and bile duct.

In some embodiments, the method further comprises determining a score for a response metric that captures change in fibrosis pattern before and following the therapy by computing a distance between distribution of fibrosis stages at baseline and following the therapy. In some embodiments, the method further comprises, based on a threshold, classifying patients as responder or non-responder to the therapy based on the score for the response metric for a respective patient.

In some embodiments, the deep learning model comprises one or more deep convolutional neural networks.

In some aspects, the described systems and methods provide for using a deep learning model to assess liver pathology, including accessing a liver pathology image associated with a patient from a group of patients in one or more randomized controlled clinical trials of nonalcoholic steatohepatitis therapy and processing, using a deep learning model, the liver pathology image to predict one or more tissue characteristic categories for at least a portion of the liver pathology image. The deep learning model may be trained on annotated liver pathology images including at least one annotation describing tissue characteristic categories for a portion of each image and may select the tissue characteristic categories from a group comprising steatosis, lobular inflammation, hepatocyte ballooning, and fibrosis stage.

In some embodiments, the method further comprises measuring a feature at or prior to the therapy of a patient, and measuring the same feature at a time point following therapy of the same patient and calculating differences in feature values to determine treatment-dependent effects.

In some embodiments, the method further comprises generating, for the liver pathology image, based on the predicted one or more tissue characteristic categories, a slide-level continuous score that corresponds to an underlying heterogeneous pattern of fibrosis observed in the liver pathology image. In some embodiments, the one or more tissue characteristic categories are predicted on a pixel-level basis. In some embodiments, the slide-level continuous score represents a continuum of severity of cellular and stromal injury to capture disease heterogeneity among different patients, wherein an ordinal classification system does not capture the disease heterogeneity among the different patients.

In some embodiments, a group comprising steatosis, lobular inflammation, and hepatocyte ballooning corresponds to components of a nonalcoholic fatty liver disease activity score (NAS). In some embodiments, for a liver pathology image, evaluating a performance of the deep learning model by comparing a fraction of tissue area in the liver pathology image assigned to each NAS component with an ordinal score determined by a pathologist, wherein the ordinal score is determined based on the NAS components. In some embodiments, intra-observer reproducibility of the ordinal score of the liver pathology image by multiple pathologists is lower than reproducibility of predictions from multiple iterations of the trained deep learning model processing the liver pathology image.

In some embodiments, the method further comprises determining a score for a response metric that captures change in fibrosis pattern before and following the therapy by computing a distance between distribution of fibrosis stages at baseline and following the therapy.

In some embodiments, the method further comprises, based on a threshold, classifying patients as responder or non-responder to the therapy based on the score for the response metric for a respective patient.

In some embodiments, the deep learning model comprises one or more deep convolutional neural networks.

Further, the inventors have developed applications for this ML-based approach to measure treatment-induced change in a clinical trial with one or multiple treatment arms. For example, the inventors' ML-based approach can be used to measure features before treatment and following treatment, and then produce a response measure based on the observed change pre-vs. post-treatment. The inventors have further developed a new metric of fibrosis response which identifies treatment effect for therapy, which was previously not identified by manual pathology scoring. In the setting of a randomized controlled trial, the inventors' ML-based approach can be used to evaluate the statistical significance of the change observed in the treatment group vs. the control group to determine treatment efficacy.

In some aspects, the described systems and methods provide for determining a score for a response metric that captures change in fibrosis pattern for a patient before and following therapy by computing a distance between distribution of fibrosis stages at baseline and following the therapy.

In some embodiments, the method further comprises, based on a threshold, classifying the patient as responder or non-responder to the therapy based on the score for the response metric for the patient.

In some embodiments, the method further comprises measuring a feature at or prior to the therapy of the patient, and measuring the same feature at a time point following therapy of the patient and calculating differences in feature values to determine treatment-dependent effects.

In some aspects, the described systems and methods provide for training a deep learning model to assess liver pathology, including accessing annotated liver pathology images associated with a group of patients in one or more randomized controlled clinical trials of nonalcoholic steatohepatitis therapy, each of the annotated liver pathology images including at least one annotation describing a stage of liver fibrosis for a portion of the image, and training the deep learning model based on the annotated liver pathology images to predict the stage of liver fibrosis for one or more portions of a liver pathology image.

In some embodiments, the stage of liver fibrosis is based on a 0 to 4 stage scale of NASH CRN system.

In some embodiments, the stage of liver fibrosis is based on a 0 to 6 stage scale of ISHAK system.

In some embodiments, the method further comprises generating, based on the predicted stage of liver fibrosis for the one or more portions of the liver pathology image, a slide-level score that corresponds to an underlying heterogeneous pattern of fibrosis observed in the liver pathology image. In some embodiments, the stage of liver fibrosis is predicted on a pixel-level basis. In some embodiments, the slide-level score is a continuous score representing a continuum of severity of cellular and stromal injury to capture disease heterogeneity among different patients, wherein an ordinal classification system does not capture the disease heterogeneity among the different patients.

In some aspects, the described systems and methods provide for using a deep learning model to assess liver pathology, including accessing a liver pathology image associated with a patient from a group of patients in one or more randomized controlled clinical trials of nonalcoholic steatohepatitis therapy and processing, using a deep learning model, the liver pathology image to predict a stage of liver fibrosis for one or more portions of the liver pathology image. The deep learning model may be trained on annotated liver pathology images including at least one annotation describing the stage of liver fibrosis for a portion of each image.

In some embodiments, the stage of liver fibrosis is based on a 0 to 4 stage scale of NASH CRN system.

In some embodiments, the stage of liver fibrosis is based on a 0 to 6 stage scale of ISHAK system.

In some embodiments, the method further comprises generating, based on the predicted stage of liver fibrosis for the one or more portions of the liver pathology image, a slide-level score that corresponds to an underlying heterogeneous pattern of fibrosis observed in the liver pathology image. In some embodiments, the stage of liver fibrosis is predicted on a pixel-level basis. In some embodiments, the slide-level score is a continuous score representing a continuum of severity of cellular and stromal injury to capture disease heterogeneity among different patients, wherein an ordinal classification system does not capture the disease heterogeneity among the different patients.

In some aspects, the described systems and methods provide for training a deep learning model to assess liver pathology, including accessing annotated liver pathology images associated with a group of patients in one or more randomized controlled clinical trials of nonalcoholic steatohepatitis therapy, each of the annotated liver pathology images including at least one annotation describing one or more histologic features of NASH for at least a portion of each image, and training the deep learning model based on the annotated liver pathology images to predict a CRN score based on a 0 to 4 stage scale of Nonalcoholic Steatohepatitis Clinical Research Network (NASH CRN) system for a liver pathology image.

In some embodiments, the one or more histologic features of NASH are selected from the group consisting of steatosis, lobular inflammation, hepatocyte ballooning, and fibrosis stage.

In some embodiments, the predicted CRN score for the liver pathology image is at least in part based on the one or more histologic features of NASH identified in the liver pathology image.

In some embodiments, the method further comprises the predicted CRN score is used to produce clinically-relevant data.

In some embodiments, the liver pathology image includes one or more trichrome whole slide images.

In some aspects, the described systems and methods provide for using a deep learning model to assess liver pathology, including accessing a liver pathology image associated with a patient from a group of patients in one or more randomized controlled clinical trials of nonalcoholic steatohepatitis therapy and processing, using a deep learning model, the liver pathology image to predict a CRN score based on a 0 to 4 stage scale of Nonalcoholic Steatohepatitis Clinical Research Network (NASH CRN) system. The deep learning model may be trained on annotated liver pathology images including at least one annotation describing one or more histologic features of NASH for at least a portion of each image.

In some embodiments, the one or more histologic features of NASH are selected from the group consisting of steatosis, lobular inflammation, hepatocyte ballooning, and fibrosis stage.

In some embodiments, the predicted CRN score for the liver pathology image is at least in part based on the one or more histologic features of NASH identified in the liver pathology image.

In some embodiments, the predicted CRN score is used to produce clinically-relevant data.

In some embodiments, the liver pathology image includes one or more trichrome whole slide images.

Further aspects of the technology may be understood based on the non-limiting illustrative embodiments described herein. While some embodiments described herein are described with respect to liver pathology, these embodiments may be equally suitable for other histology or pathology applications.

Still other aspects, embodiments, and advantages of these exemplary aspects and embodiments, are discussed in detail below. Any embodiment disclosed herein may be combined with any other embodiment in any manner consistent with at least one of the objects, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF THE DRAWINGS

Various aspects of at least one embodiment are discussed below with reference to the accompanying figures, which are not intended to be drawn to scale. Where technical features in the figures, detailed description or any claim are followed by reference signs, the reference signs have been included for the sole purpose of increasing the intelligibility of the figures, detailed description, and claims. Accordingly, neither the reference signs nor their absence is intended to have any limiting effect on the scope of any claim elements. For purposes of clarity, not every component may be labeled in every figure. The figures are provided for the purposes of illustration and explanation and are not intended as a definition of the limits of the systems and methods described herein. In the figures:

DETAILED DESCRIPTION

The systems and methods developed by the inventors leverage deep convolutional neural networks (dCNNs) for quantitative tissue characterization to improve upon existing histologic evaluation techniques by, increasing reproducibility, identifying novel pathologic features relevant for patient outcomes, and providing a platform for rigorous assessment of patient disease progression. Accordingly, some embodiments provide for training and applying an ML-based approach to assess histology and fibrosis using slides from multiple randomized controlled trials of advanced NASH fibrosis and compensated NASH cirrhosis. The models can recapitulate the fibrosis stage and other patient histologic features assessed by a central pathologist. These models can be further used to characterize the heterogeneity of fibrosis that exists within a given biopsy. Histologic assessment of NAS and fibrosis features by the model can be superior to a composite score defined by expert pathologists in terms of agreement with consensus and in clinical utility for prediction of outcomes. The inventors have further developed the ability to use the model to track response to therapy. For example, the system may measure a feature at or prior to the therapy of a patient and, at a time point following therapy of the same patient, measure the same feature and calculate differences in feature values to determine treatment-dependent effects. The inventors have recognized the power of an ML-based approach to liver pathology and have developed this approach for risk stratification and for assessing the effect of new therapies in NASH.

Throughout this disclosure, a convolutional neural network is used as an exemplary basis for a deep learning model that may be used in accordance with some embodiments. However, it should be appreciated that other types of statistical models may alternatively be used, and embodiments are not limited in this respect. Other types of statistical models that may be used include a support vector machine, a neural network, a graph neural network, a regression model, a random forest, a clustering model, a Bayesian network, reinforcement learning, metric learning, a genetic algorithm, or another suitable statistical model. More details for training the convolutional neural network are provided with respect to FIG. 4.

In some aspects, the described systems and methods provide for a method for training a deep learning model to assess liver pathology. This method may be implemented on a computer system, such as system 500 discussed with respect to FIG. 5, or another suitable computer system, or a combination thereof. The system may access a plurality of annotated liver pathology images associated with a group of patients in one or more randomized controlled clinical trials of nonalcoholic steatohepatitis therapy. Each of the plurality of annotated liver pathology images may include at least one annotation describing one or more tissue characteristic categories for a portion of the image. The system may train the deep learning model based on the plurality of annotated liver pathology images to predict the one or more tissue characteristic categories for a liver pathology image. The tissue characteristic categories may be selected from a group comprising steatosis, lobular inflammation, hepatocyte ballooning, and fibrosis stage, or another suitable tissue characteristic category. The system may store the trained deep learning model on at least one storage device. In some embodiments, the deep learning model comprises one or more deep convolutional neural networks.

In some embodiments, a group comprising steatosis, lobular inflammation, and hepatocyte ballooning corresponds to components of a nonalcoholic fatty liver disease activity score (NAS). In some embodiments, for a liver pathology image, the system evaluates a performance of the deep learning model by comparing a fraction of tissue area in the liver pathology image assigned to each NAS component with an ordinal score determined by a pathologist, wherein the ordinal score is determined based on the NAS components. In some embodiments, intra-observer reproducibility of the ordinal score of the liver pathology image by multiple pathologists is lower than reproducibility of predictions from multiple iterations of the trained deep learning model processing the liver pathology image.

In some embodiments, the system may process, using the trained deep learning model, a liver pathology image to generate predicted one or more tissue characteristic categories for the liver pathology image and generate, for the liver pathology image, based on the predicted one or more tissue characteristic categories, a slide-level continuous score that corresponds to an underlying heterogeneous pattern of fibrosis observed in the liver pathology image.

In some embodiments, the tissue characteristic categories are predicted on a pixel-level basis. In some embodiments, the slide-level continuous score represents a continuum of severity of cellular and stromal injury to capture disease heterogeneity among different patients, wherein an ordinal classification system does not capture the disease heterogeneity among the different patients.

In some embodiments, the system extracts values for a plurality of complex features from each of the annotated liver pathology images and trains the deep learning model based on the plurality of annotated liver pathology images and the values for the plurality of complex features. The plurality of complex features may include one or more features not included in the NAS components. In some embodiments, the plurality of complex features comprises at least one ratio of the NAS components, including a ratio of area of hepatocellular ballooning to steatosis. In some embodiments, the one or more features not included in the NAS components include portal inflammation and bile duct.

In some embodiments, the system determines a score for a response metric that captures change in fibrosis pattern before and following the therapy by computing a distance between distribution of fibrosis stages at baseline and following the therapy. In some embodiments, based on a threshold, the system classifies patients as responder or non-responder to the therapy based on the score for the response metric for a respective patient. In some embodiments, the system may measure a feature at or prior to the therapy of a patient, and measure the same feature at a time point following therapy of the same patient and calculate differences in feature values to determine treatment-dependent effects.

Exemplary Implementation

Further aspects of the technology may be understood based on the non-limiting illustrative embodiments described further below. Examples of specific implementations are provided herein for illustrative purposes only and are not intended to be limiting. While some embodiments described herein are described with respect to liver pathology, these embodiments may be equally suitable for other histology or pathology applications.

Data Sets: For example, samples from randomized controlled trials of therapeutics for NASH may be obtained for training and testing. The data sets may relate to patients in a suitable age range, e.g., between 18 to 70 years of age, with a histologic diagnosis of NASH (e.g., presence of at least grade 1 steatosis, hepatocellular ballooning, and lobular inflammation). For example, the data sets may relate to patients with bridging fibrosis (F3), compensated cirrhosis (F4), or another suitable diagnosis. Patients may be deemed to have a clinical event if they had evidence of hepatic decompensation (e.g., ascites, hepatic encephalopathy of grade 2 or higher, or gastrointestinal bleeding secondary to portal hypertension), or whose hepatic function worsened to the level that would make them eligible to be listed for liver transplantation (MELD ≥15), who progressed to cirrhosis based on histology, or another suitable clinical event.

Construction of Training, Validation, and Testing Datasets:

To develop a dataset for model development the system may split the slides into training, validation and testing splits. In one example, using a network of expert pathologists, the system may collect pathologist expert annotations on H&E and Trichrome images for supervised model training.

Figure 1:
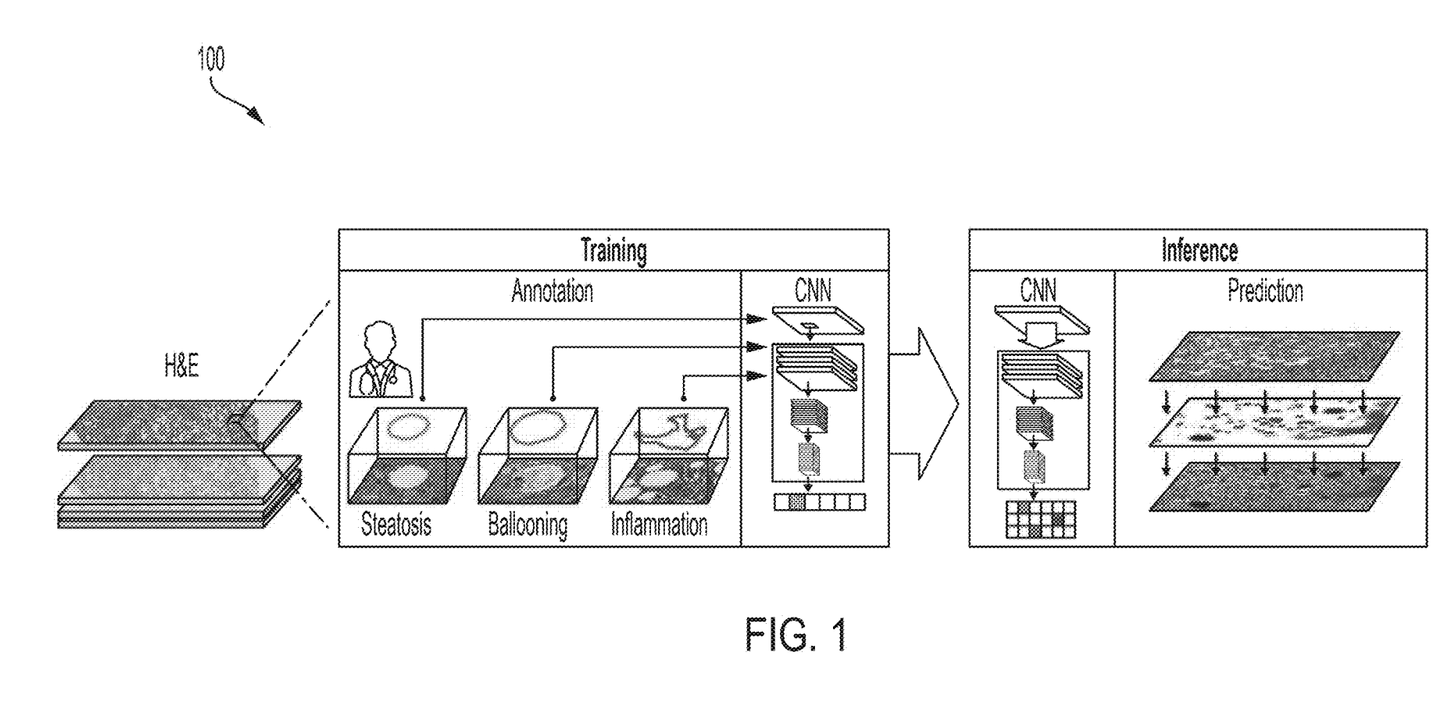
FIG. 1 shows aspects of an ML system for quantification of NAS features, in accordance with some embodiments of the technology described herein.

Training an ML System for Quantification of the NAS Components:

In some embodiments, using the H&E slide images and annotations, the system may train a dCNN to produce pixel level predictions of NAS components (steatosis, lobular inflammation, ballooning; FIG. 1). FIG. 1 shows aspects of an ML system 100 for quantification of NAS features in accordance with some embodiments of the technology described herein, including the H&E slide images (left panel), an ML process for training and deploying models for the NAS (middle panel; example pathologist annotations shown via bounding boxes), and these annotations being used for model training to generate pixel-resolution heatmaps which segment the tissue into corresponding regions (right panel). The model may be trained until convergence is achieved and model selection may be performed using performance on held out pathologist annotations on the validation set. In some embodiments, the deep convolutional neural networks may be trained to recognize specific tissue morphologies within a whole slide image using the pathologist-derived annotations (see FIG. 1). For example, these models may comprise 8-12 blocks of compound layers with a topology inspired by residual networks and inception networks with a softmax loss. Whole slide image annotations may be grouped into classes as appropriate and then used to generate training sets of image patches, e.g., on the order of 100 k-500 k samples, or another suitable number. These may then be used to train the model with stochastic minibatch gradient descent using the ADAM optimizer algorithm, or another suitable algorithm. Model training may be monitored and hyperparameters adjusted based on the performance of the model on patches derived from annotations on whole slide images in the validation set.

The system may evaluate the model by comparing the fraction of tissue area assigned to each NAS component in the test set with the ordinal score as determined by the central pathologist. The inventors have found model predictions to be significantly correlated with ordinal scores for all three NAS components across all test set slides, with similar performance across all individual trials used. Importantly, model performance did not degrade on slides from the test data, despite its exclusion from the training data set. To visualize the output of the models, the system may create heatmaps representing the ML-based prediction of the NAS components and visualize the predictions on the H&E-stained images.

In some embodiments, to examine the reliability and reproducibility of pathologist scoring, independent expert liver pathologists may score each slide. The inventors have found that pathologist scoring of NAS features show only moderate intra-observer reproducibility. Specifically, intra-pathologist agreement for repeated pathologist scores on the same slide may be lower than repeatedly generated model predictions on the same image. A significant advantage of a machine learning-based approach may be reproducibility with similar or identical agreement of scores from multiple runs of the same algorithm on the same image.

Figure 2:
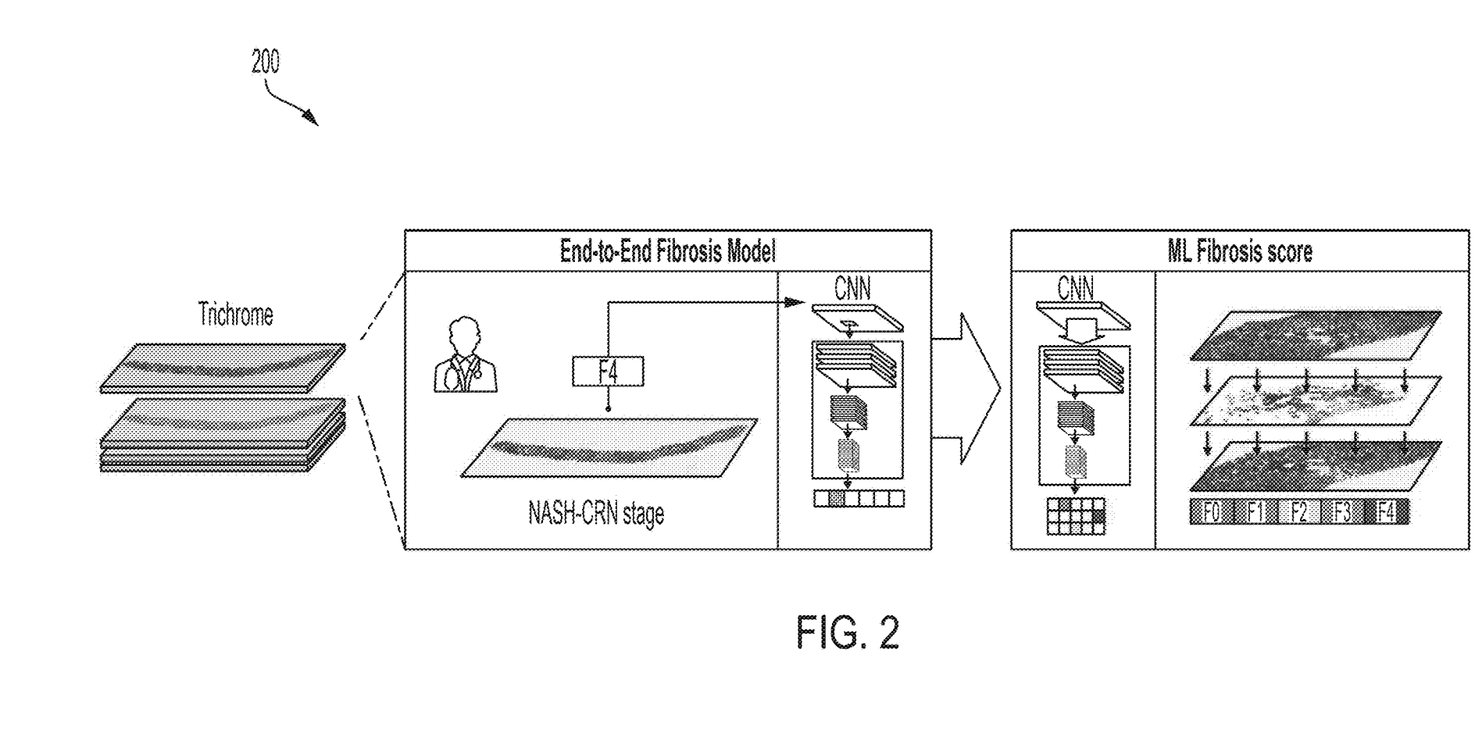
FIG. 2 shows aspects of an ML system for staging of fibrosis, in accordance with some embodiments of the technology described herein.

Training an ML System for Quantification of Fibrosis:

In some embodiments, the inventors have developed an "end to end" (E2E) model (FIG. 2) for staging of fibrosis from trichrome stained slides, which was trained using the central pathologist slide stage and learned to predict the stage from regions of fibrosis in the image. FIG. 2 shows aspects of an ML system 200 for staging of fibrosis in accordance with some embodiments of the technology described herein, including the trichrome stained slides (left panel), an ML process for training and deploying models for fibrosis staging where a model is trained using the central pathologist's ordinal fibrosis stage (NASH CRN 0-4 and ISHAK 0-6, middle panel), and the model performing pixel wise prediction where these predictions are pooled over the entire slide to yield a per-slide prediction and distribution of fibrosis stages (right panel). To produce slide-level predictions, the system may compute a pixel-wise classification of each region of fibrosis and take the weighted average of these predictions to generate a single slide-level continuous score that summarizes the underlying heterogeneous pattern of fibrosis observed in a single liver biopsy. On testing set slides, this score may be concordant with central pathologist fibrosis staging. Concordance of this score may be consistent in the testing set in each trial, demonstrating model generalization across slide collection sites.

In addition to an accurate reproduction of manual patient fibrosis staging, the model's point wise predictions of overall ISHAK and CRN score may enable a continuous measure of disease severity. The inventors have recognized that this measure illuminates previously unappreciated patient disease heterogeneity which is not captured by the signal ordinal score provided by traditional manual pathologists scoring using either the CRN or ISHAK staging systems.

ML-Powered Pathology to Assess Prognosis:

In some embodiments, to assess the prognostic value of continuous ML-generated measures of NASH histology in comparison to manual scores, the system may compute the c-statistic for each feature to indicate its association with progression to cirrhosis, clinical events, or another suitable diagnosis. For NAS features and ISHAK fibrosis staging, the inventors have found the ML-generated features to be as prognostic or more prognostic than the central pathologist-generated feature.

In addition to recapitulating human scoring criteria, ML models may enable quantification of more complex features, such as ratios of NAS features (e.g., Ratio of area of hepatocellular ballooning to steatosis) and features not included in the NAS features (e.g., portal inflammation, bile duct). The system may use these features to identify novel histological biomarkers associated with disease progression or clinical events. For example, the system may find feature clusters which are significantly associated with progression in the data sets. For example, the cluster may include features capturing the ratio of hepatocellular ballooning to steatosis; patients with more ballooning and less steatosis at baseline were significantly more likely to have disease progression to cirrhosis or a clinical event. In another example, the cluster may include features capturing portal inflammation, where patients with high levels of portal inflammation (e.g., top quartile) may be significantly more likely to progress to cirrhosis or to clinical events.

Figure 3:
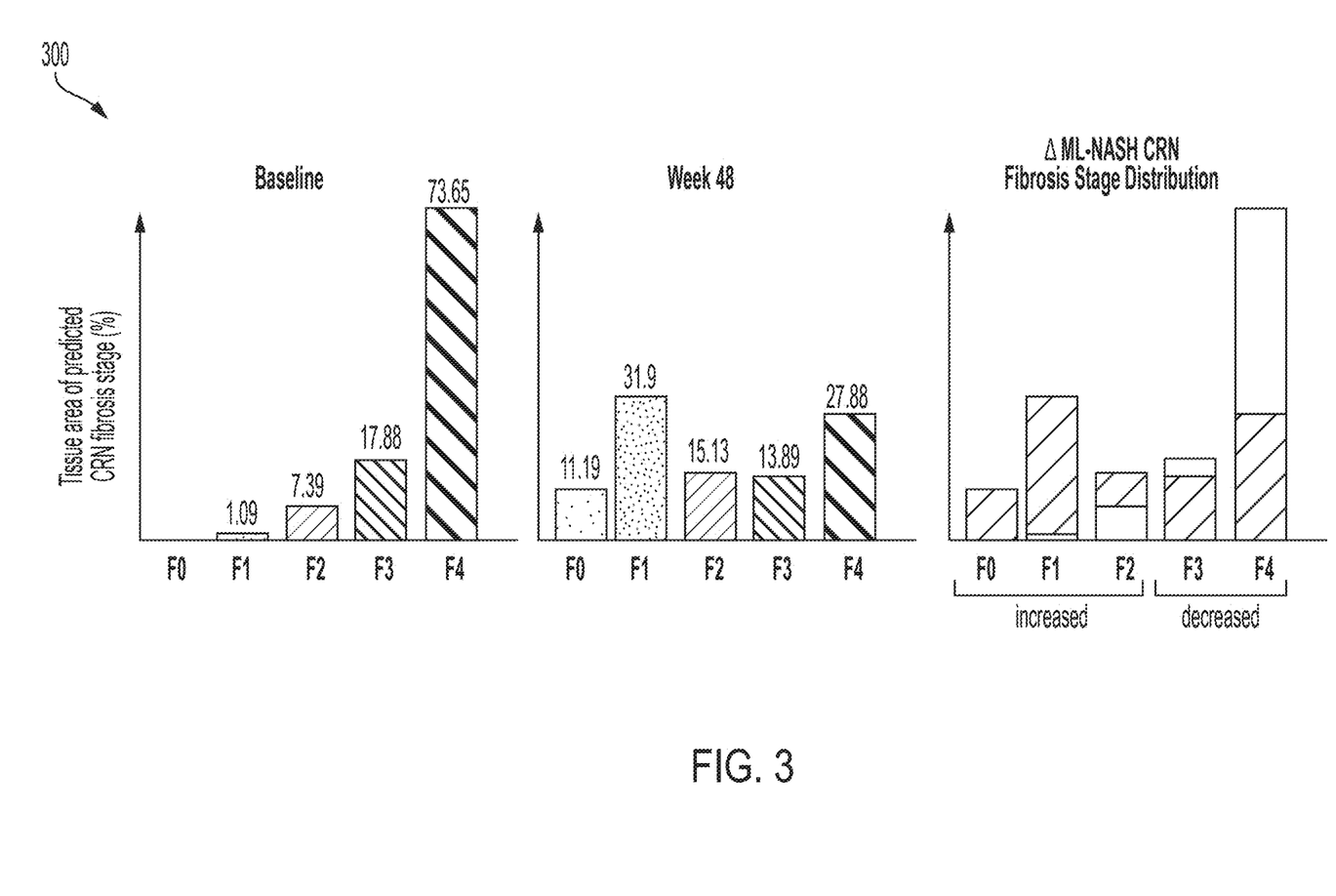
FIG. 3 shows example quantification of changes in fibrosis from advanced (F3-F4) to less advanced (≤F2) fibrosis stage patterns for a patient treated with therapy in a randomized controlled trial, in accordance with some embodiments of the technology described herein.

Monitoring of Treatment Response with Machine Learning Features:

Beyond use for subject inclusion, pathology may play a critical role in NASH clinical trials for the assessment of changes in pathologic phenotypes in response to treatment. Indeed, histological review of fibrosis is a central component of currently accepted endpoints for clinical trials in NASH. While traditional staging by the NASH CRN or ISHAK fibrosis classifications include only a single integer measurement of fibrosis, the ML method may enable quantification of a distribution of fibrosis patterns (FIG. 3; 300). The inventors have found that considering the change in the full distribution of fibrosis patterns within a patient's liver biopsy may provide a more sensitive measure of biological change following treatment with an effective therapy. To this end, the inventors have developed a metric based on the Wasserstein probability distribution metric, termed the DELTA (Deep Learning Treatment Assessment) Liver Fibrosis score that captures the change in fibrosis patterns before and after treatment. Specifically, the score is the $1^{st}$ Wasserstein distance (or earth mover's distance) between the distribution of fibrosis stages at baseline and following treatment multiplied by the overall shift in mean score between timepoints. The Wasserstein distance measures the amount of "work" required to turn one distribution into another; in this case, the magnitude of change in the composition of predicted NASH CRN fibrosis stages between baseline and a later time (e.g., as shown between baseline and week 48 in FIG. 3). The Wasserstein distance is symmetric and unitless (i.e. the amount of work is the same regardless of direction); therefore, the system may scale by the mean to give the DELTA score a sign and an interpretable magnitude.

To evaluate the clinical relevance of this metric, the association between the DELTA Liver Fibrosis score with histological progression to cirrhosis among patients with bridging (F3) fibrosis may be evaluated. The inventors found that patients who progressed to cirrhosis had a greater DELTA Liver Fibrosis score from a baseline initial time point to a later time point compared with patients who did not progress to cirrhosis (e.g., Mann-Whitney p<0.001).

In some embodiments, the system evaluates the utility of the DELTA Liver Fibrosis score for monitoring treatment effects. For example, a therapy may lead led to improvement in histological and noninvasive measures of fibrosis and liver injury compared with placebo over a period of time. However, the difference between the therapy and placebo for the primary endpoint (fibrosis improvement without worsening of NASH) may not be statistically significant, potentially due to insensitivity of manual pathological review. To address this, the system may evaluate concordance between the DELTA Liver Fibrosis score and standard pathological staging of fibrosis. First, the system may assess whether patients treated with the therapy who achieved a ≥1-stage improvement in fibrosis by the NASH CRN classification according to central pathologist review showed a significant decrease in the DELTA Liver Fibrosis score. For example, therapy-treated patients with a fibrosis response may have a greater reduction in DELTA Liver Fibrosis score compared with fibrosis non-responders.

Because the DELTA Liver Fibrosis score is more sensitive than manual pathological staging for the identification of treatment effects, a greater reduction may be identified in DELTA Liver Fibrosis score in therapy-treated patients versus placebo-treated patients who had a fibrosis response because the latter may be more likely to be due to sampling variability of liver biopsy. For example, among patients deemed to have a fibrosis response by manual pathological staging, those treated with the therapy may have significantly greater reductions in DELTA Liver Fibrosis score compared to placebo-treated patients, in whom scores were not different between responders and non-responders. In order to validate this differential in DELTA Liver Fibrosis score via non-histological measures, the inventors have compared changes in scores between patients with and without reductions of the noninvasive fibrosis markers, Enhanced Liver Fibrosis score (ELF; Siemens, Tarrytown, NY) and liver stiffness by transient elastography (FibroScan; Echosens, Paris, France) between baseline and at a later time. In patients with advanced fibrosis due to NASH, changes of this magnitude have been associated with a reduced risk of clinical disease progression. For example, therapy-treated patients with reductions in both measures may have lower DELTA Liver Fibrosis scores than non-responders (e.g., ELF score, liver stiffness), confirming the relevance of this metric for monitoring disease severity.

In some embodiments, a threshold of the DELTA Liver Fibrosis score may be defined in order to classify patients as fibrosis responders or non-responders. For example, in randomized controlled trials of NASH therapies, approximately 20% of patients treated with placebo may achieve a ≥1-stage improvement in fibrosis. This high placebo response may be a challenge for adequately powering clinical trials, e.g., smaller phase 2 studies. In one example, to create a stringent threshold, the 10th percentile of DELTA Liver Fibrosis score in all patients may be identified, which would be expected to reduce the fibrosis response rate by one-half among placebo-treated patients. The value of the 10th percentile of DELTA Liver Fibrosis score may then be applied to data to classify patients as responders or non-responders. Using this threshold, a higher proportion of patients treated with the therapy may be classified as responders compared with the proportion of patients treated with placebo classified as responders. In contrast, using manual pathological staging, the proportion of patients with a ≥1-stage improvement in fibrosis may not be statistically different between therapy-treated and placebo-treated patients. Therefore DELTA Liver Fibrosis may be a more accurate and sensitive metric than manual pathological staging of fibrosis for identifying the effects of treatment in patients with NASH.

Any suitable imaging instrument may be used to obtain a pathology image, a histology image, or a tissue image, e.g., from a tissue sample on a slide. In some embodiments, a suitable imaging instrument includes an Olympus BX41 microscope in combination with a DP21 2 MP camera and CellSens software all available from Olympus Corporation (Center Valley, PA). Another suitable imaging instrument includes the Aperio ScanScope CS-0, Aperio AT2, and Aperio eSlide manager and web browser all available from Leica Biosystems, Inc. (Buffalo Grove, IL). Stained images may be acquired using, for example, a high resolution whole-slide scanner such as the Nanozoomer Whole Slide Scanner from Hamamatsu (Hamamatsu City, Shizuoka Pref., Japan). Once the images are acquired, either for training data or from a test sample, the image data may be provided to a system configured to process the image data using, for example, a statistical model.

For pathologist data acquisition, pathology images may be presented to a panel of pathologists using, e.g., a web-based platform. Pathologists may be given annotation instructions and tasked with identifying (and/or exhaustively marking) all cells of a given type within each image. For example, data may be collected for tissue characteristics including, but not limited to, steatosis, lobular inflammation, hepatocyte ballooning, and fibrosis stage. In some embodiments, the results are shown to one or more pathologists via a user interface through which the pathologist can identify cells. The pathologist may provide reference annotations for regions (e.g., in the form of polygon annotations) or cells (e.g., in the form of point annotations) in a pathology image. The tissue or cellular characteristic category of the annotations may be specified to the pathologist, and input requested only for annotations of the specified tissue or cellular characteristic category, to ensure that the data is collected in a structured way instead of pathologists simply inputting text, e.g., tissue or cellular characteristic category, for each annotation they provide. For example, a user interface configured to display the pathology image may provide a drop down menu and/or a selection tool that enables the pathologist to select from among a fixed set of tissue or cellular characteristic categories.

Pathology images, histology images, or tissue images described herein may be microscopic images of tissue samples extracted from a patient. The images may be obtained by using an imaging instrument to create images of slides on which tissue slices are mounted. For example, the tissue slices mounted on the slides may have been taken from tissue samples, such as biopsy or autopsy specimens or tissue resections. The tissue samples may have been processed prior to capturing of images. For example, the tissue samples may have been fixed, stained, labeled, washed, or dehydrated. The samples may be taken from any tissue that indicates the presence or absence of a pathological condition. For example, the image may include a portion of a tumor. The image may be of a tissue that provides evidence of the presence or absence of a disease or condition, such as cancer, Alzheimer's disease, Parkinson's disease, diabetes, cystic fibrosis, sickle cell anemia, or an autoimmune disease. For example and without limitation, the tissue may be from a tumor or from the liver, lung, breast, ovary, uterus, cervix, vagina, testicle, spleen, lymph node, bladder, kidney, brain, esophagus, stomach, intestine, gall bladder, mouth, lip, nose, pancreas, prostate, colon, skin, or any other organ that may be suspected of having a tumor.

Tissue samples may include biopsied tissue obtained, for example, through core needle biopsy. The samples may be paraffin-embedded and may be sectioned into slices prior to staining. Tissue samples may be stained using any stain selected to highlight cellular structures or other features of interest useful in tissue analysis. The tissue samples may, for example, be prepared by hematoxylin and eosin stain (H&E stain). Examples of general staining methods include, but are not limited to, hematoxylin and eosin (H&E), trichrome, periodic acid Schiff (PAS), autoradiography, enzyme histochemistry, immuno-fluorescence, and immunohistochemistry (IHC). Specific stains include, but are not limited to, acid fuchsin, Aldehyde Fuchsin, Alician Blue, Alizarin Red S, Alkaline Phosphatase, aniline blue, Azan Stain, biebrich scarlet, Bielschowsky Stain, Cajal Stain, chromotrope 2R, Congo Red, Cresyl Violet, Eosin, fast green FCF, Fontana-Masson, Giemsa Stain, Golgi Stain, Gomori Trichrome, Heidenhain's AZAN trichrome stain, Hematoxylin, Iron Hematoxylin, light green SF yellowish, Luna Stain, Luxol Fast Blue, Mallory Trichrome, martius yellow, Masson Trichrome, Melanin Stains, methyl blue, milling yellow, Movat's Pentachrome, Mucicarmine, Mucin Stains, Myeloperoxidase (MPO), Nissl Stains, Nuclear Fast Red, Oil Red 0, orange G, Orcien Stain, Osmium Tetroxide, Papanicolaou Stain, Perl's Iron Stain, phloxine, Phosphotungstic Acid-Hematoxylin (PTAH), picric acid, PicroSirius Red (polarized), ponceau 6R, Prussian Blue, Reticular Fiber Stain, Romanowsky Stains, Safranin 0, Schmorl's Stain, Silver Stains, Sudan Stains, Tartrazine, tartrazine, Toluidine Blue, Van Gieson, Verhoeff Stain, Von Kassa Stain, water blue, Weigert's Elastic Stain, Wright's Stain, and xylidine ponceau.

The tissue samples may be immune-stained with anti-cytokeratin antibody. The tissue samples may be prepared by yet other methods. For example, a tissue sample may be prepared by Papanicolaou stain (Pap stain). A sample could optionally be labeled by antibodies or probes, e.g., either of which could be fluorescently labeled or conjugated to elemental isotopes for mass spectrometry. Tissue staining may comprise IHC staining using, for example, labelled antibodies targeting proteins of interest or primary followed by secondary antibodies where the primary antibodies target proteins of interest and the secondary antibodies target the primary antibodies and carry, for example, a fluorescent or otherwise reporter detectable through known imaging techniques. Tissue staining such as immunohistochemistry may be performed on an automated platform such as those available from Ventana Medical Systems, Inc. (Tucson, Arizona). Tissue sample images may be captured using an imaging instrument such as a microscope and digital camera and corresponding software.

Drug Development Tool for Assessing Clinical Trial Endpoints:

In some embodiments, the inventors have recognized that limitations of manual pathology may confound results of NASH clinical trials. In order to address these limitations, the inventors have developed an AI-based drug development tool (herein referred to as AIM-NASH) that can reproducibly calculate NASH Clinical Research Network (CRN) scores. This tool may be implemented using any of the systems and methods described herein.

In a non-limiting example, machine learning models were developed using 5923 biopsies from six phase 2b or 3 trials in NASH subjects with F1-F4 fibrosis. Models were trained to identify NASH histologic features and predict ordinal CRN scores using >100 k annotations from expert pathologists. Analytic performance was tested in a held-out dataset of 639 H&E- and 633 trichrome-stained biopsy images (NCT02784444; EMINENCE). Agreement between AIM-NASH scores and the consensus of three expert hepatopathologists was evaluated using linearly-weighted Kappa (k) statistics. Histologic endpoints were retrospectively assessed by AIM-NASH and central reader scores from a separate phase 2b trial (NCT03449446; ATLAS). Comparisons of treatment responses between groups were made using the Mantel-Haenszel test, stratified by diabetes and cirrhosis status.

The inventors found that agreement between AIM-NASH and consensus reads was higher than that among pathologists [AIM-NASH steatosis k=0.71 (95% CI 0.67-0.74) vs mean pairwise inter-pathologist steatosis k=0.60 (0.56-0.63); lobular inflammation k=0.50 (0.45-0.55) vs 0.33 (0.29-0.37); ballooning k=0.58 (0.53-0.63) vs 0.48 (0.44-0.52); fibrosis k=0.58 (0.54-0.62) vs 0.50 (0.47-0.53)]. In ATLAS, AIM-NASH identified more responders vs. the central reader in subjects treated with cilofexor and firsocostat for ≥1-stage fibrosis improvement without NASH worsening (26% vs 21%), NASH resolution without fibrosis worsening (16% vs 5%), and >2-point reduction in NAS (68% vs 38%), and greater improvements in treated subjects vs placebo (see Table 1).

Accordingly, AIM-NASH may enable automated, and sensitive ML-based CRN scoring, and generate reproducible assessments of disease activity from biopsy samples. AIM-NASH may potentially support standardized evaluation of histologic endpoints in NASH clinical trials.

TABLE 1

AIM-NASH and Central Reader Assessments of Treatment Response in ATLAS (F3-F4)

| Endpoints* | AIM-NASH | | | Central Reader | | |
|---|---|---|---|---|---|---|
| | CILO + FIR | Placebo | P-value | CILO + FIR | Placebo | P-value |
| Fibrosis improvement without NASH worsening | 26% (16/61) | 13% (4/32) | 0.142 | 21% (13/63) | 11% (4/38) | 0.190 |
| NASH resolution without fibrosis worsening | 16% (9/55) | 7% (2/27) | 0.212 | 5% (3/63) | 0% (0/38) | 0.332 |
| ≥2-pt reduction in NAS | 68% (40/59) | 27% (8/30) | <0.001 | 38% (24/64) | 11% (4/38) | 0.001 |

*Sample size for each endpoint varies due to data availability.
CILO, cilofexor; FIR, firsocostat; NAS, NAFLD Activity Score.

Exemplary Model Architecture

Figure 4:
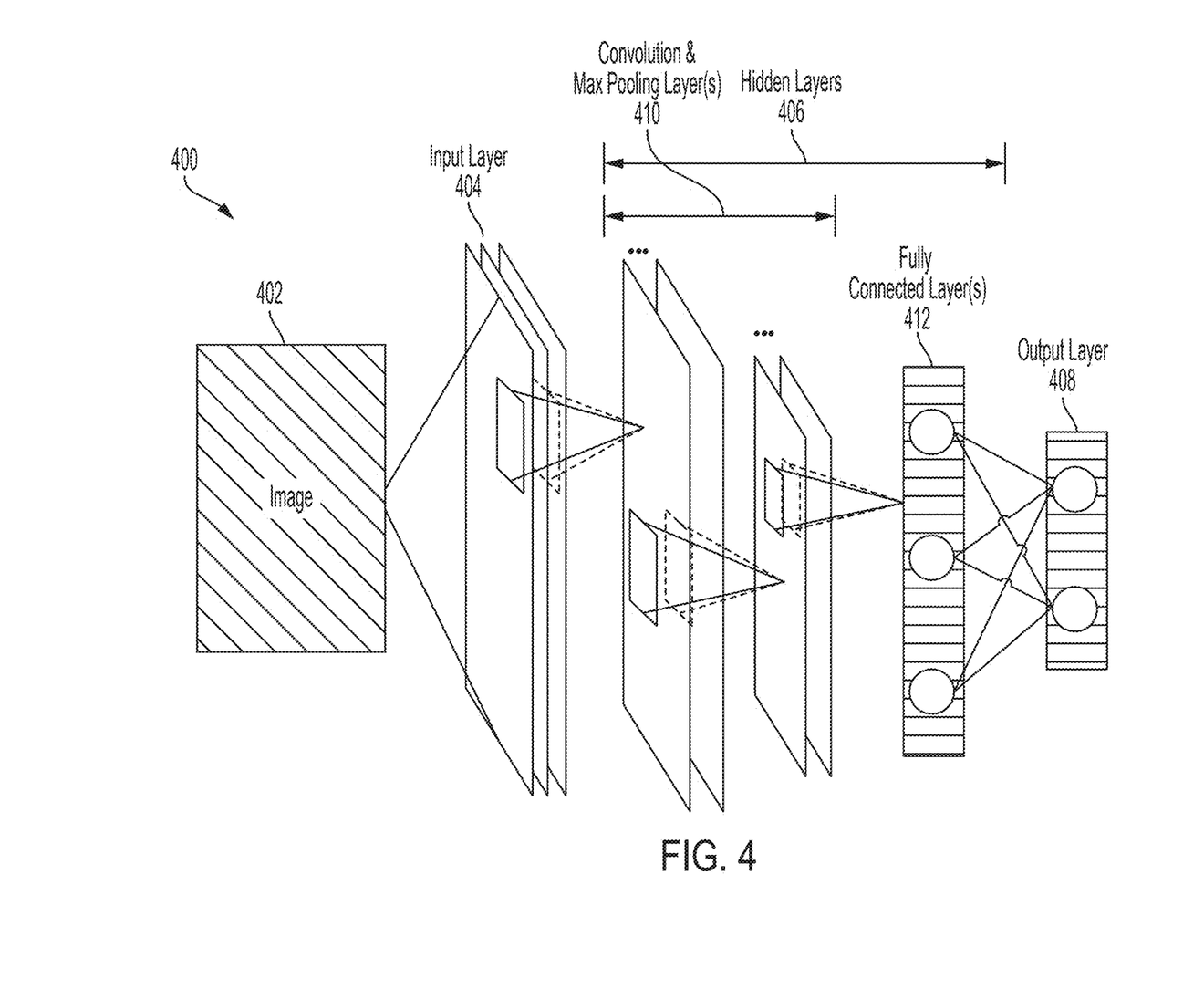
FIG. 4 schematically shows layers of a convolutional neural network, in accordance with some embodiments of the technology described herein.

In some embodiments, the deep learning model may include a convolutional neural network. The convolutional neural network may be fully convolutional or may have one or more fully connected layers. In some embodiments, the model may be a different type of neural network model such as, for example, a recurrent neural network, a multi-layer perceptron, and/or a restricted Boltzmann machine. It should be appreciated that the model is not limited to being implemented as a neural network and, in some embodiments, may be a different type of model that may be used to predict annotations for one or more portions of a pathology image. For example, the model may be any suitable type of nonlinear regression model such as a random forest regression model, a support vector regression model, or an adaptive basis function regression model. As another example, the model may be a Bayesian regression model or any other suitable Bayesian Hierarchical model. In some embodiments, a neural network includes an input layer, an output layer, and one or more hidden layers that define connections from the input layer to the output layer. Each layer may have one or more nodes. For example, the neural network may include at least 5 layers, at least 10 layers, at least 15 layers, at least 20 layers, at least 25 layers, at least 30 layers, at least 40 layers, at least 50 layers, or at least 100 layers. FIG. 4 provides details for training a convolutional neural network in accordance with some embodiments for model predictions of annotations for pathology images using the training data.

In some embodiments, the deep learning model can be implemented based on a variety of topologies and/or architectures including deep neural networks with fully connected (dense) layers, Long Short-Term Memory (LSTM) layers, convolutional layers, Temporal Convolutional Layers (TCL), or other suitable type of deep neural network topology and/or architecture. The neural network can have different types of output layers including output layers with logistic sigmoid activation functions, hyperbolic tangent activation functions, linear units, rectified linear units, or other suitable type of nonlinear unit. Likewise, the neural network can be configured to represent the probability distribution over n different classes via, for example, a softmax function or include an output layer that provides a parameterized distribution e.g., mean and variance of a Gaussian distribution.

FIG. 4 schematically shows layers of a convolutional neural network 400 in accordance with some embodiments of the technology described herein. Convolutional neural network 400 may be used to predict annotations for a pathology image in accordance with some embodiments of the technology described herein. For example, convolutional neural network 400 may be used to predict annotations for a pathology image. The convolutional neural network may be used because such networks are suitable for analyzing visual images. The convolutional neural network may require no pre-processing of a visual image in order to analyze the visual image. As shown, the convolutional neural network comprises an input layer 404 configured to receive information about the image 402 (e.g., pixel values for all or one or more portions of a pathology image), an output layer 408 configured to provide the output (e.g., a classification), and a plurality of hidden layers 406 connected between the input layer 404 and the output layer 408. The plurality of hidden layers 406 include convolution and pooling layers 410 and fully connected layers 412.

The input layer 404 may be followed by one or more convolution and pooling layers 410. A convolutional layer may comprise a set of filters that are spatially smaller (e.g., have a smaller width and/or height) than the input to the convolutional layer (e.g., the image 402). Each of the filters may be convolved with the input to the convolutional layer to produce an activation map (e.g., a 2-dimensional activation map) indicative of the responses of that filter at every spatial position. The convolutional layer may be followed by a pooling layer that down-samples the output of a convolutional layer to reduce its dimensions. The pooling layer may use any of a variety of pooling techniques such as max pooling and/or global average pooling. In some embodiments, the down-sampling may be performed by the convolution layer itself (e.g., without a pooling layer) using striding.

The convolution and pooling layers 410 may be followed by fully connected layers 412. The fully connected layers 412 may comprise one or more layers each with one or more neurons that receives an input from a previous layer (e.g., a convolutional or pooling layer) and provides an output to a subsequent layer (e.g., the output layer 408). The fully connected layers 412 may be described as "dense" because each of the neurons in a given layer may receive an input from each neuron in a previous layer and provide an output to each neuron in a subsequent layer. The fully connected layers 412 may be followed by an output layer 408 that provides the output of the convolutional neural network. The output may be, for example, an indication of which class, from a set of classes, the image 402 (or any portion of the image 402) belongs to. The convolutional neural network may be trained using a stochastic gradient descent type algorithm or another suitable algorithm. The convolutional neural network may continue to be trained until the accuracy on a validation set (e.g., held out images from the training data) saturates or using any other suitable criterion or criteria.

It should be appreciated that the convolutional neural network shown in FIG. 4 is only one example implementation and that other implementations may be employed. For example, one or more layers may be added to or removed from the convolutional neural network shown in FIG. 4. Additional example layers that may be added to the convolutional neural network include: a pad layer, a concatenate layer, and an upscale layer. An upscale layer may be configured to upsample the input to the layer. An ReLU layer may be configured to apply a rectifier (sometimes referred to as a ramp function) as a transfer function to the input. A pad layer may be configured to change the size of the input to the layer by padding one or more dimensions of the input. A concatenate layer may be configured to combine multiple inputs (e.g., combine inputs from multiple layers) into a single output.

As another example, in some embodiments, one or more convolutional, transpose convolutional, pooling, unpooling layers, and/or batch normalization may be included. As yet another example, the architecture may include one or more layers to perform a nonlinear transformation between pairs of adjacent layers. The non-linear transformation may be a rectified linear unit (ReLU) transformation, a sigmoid, and/or any other suitable type of non-linear transformation, as aspects of the technology described herein are not limited in this respect. In some embodiments, any suitable optimization technique may be used for estimating neural network parameters from training data. For example, one or more of the following optimization techniques may be used: stochastic gradient descent (SGD), mini-batch gradient descent, momentum SGD, Nesterov accelerated gradient, Adagrad, Adadelta, RMSprop, Adaptive Moment Estimation (Adam), AdaMax, Nesterov-accelerated Adaptive Moment Estimation (Nadam), AMSGrad.

Convolutional neural networks may be employed to perform any of a variety of functions described herein. For example, a convolutional neural network may be employed to predict tissue or cellular characteristics for a pathology image. It should be appreciated that more than one convolutional neural network may be employed to make predictions in some embodiments. For example, a first convolutional neural network may be trained on a set of annotated pathology images and a second, different convolutional neural network may be trained on the same set of annotated pathology images, but magnified by a particular factor, such as 5×, 10×, 20×, or another suitable factor. The first and second neural networks may comprise a different arrangement of layers and/or be trained using different training data. In some embodiments, the convolutional neural network does not include padding between layers. The layers may be designed such that there is no overflow as pooling or convolution operations are performed. Moreover, layers may be designed to be aligned. For example, if a layer has an input of size N*N, and has a convolution filter of size K, with stride S, then (N-K)/S must be an integer in order to have alignment.

Exemplary Computer Architecture

Figure 5:
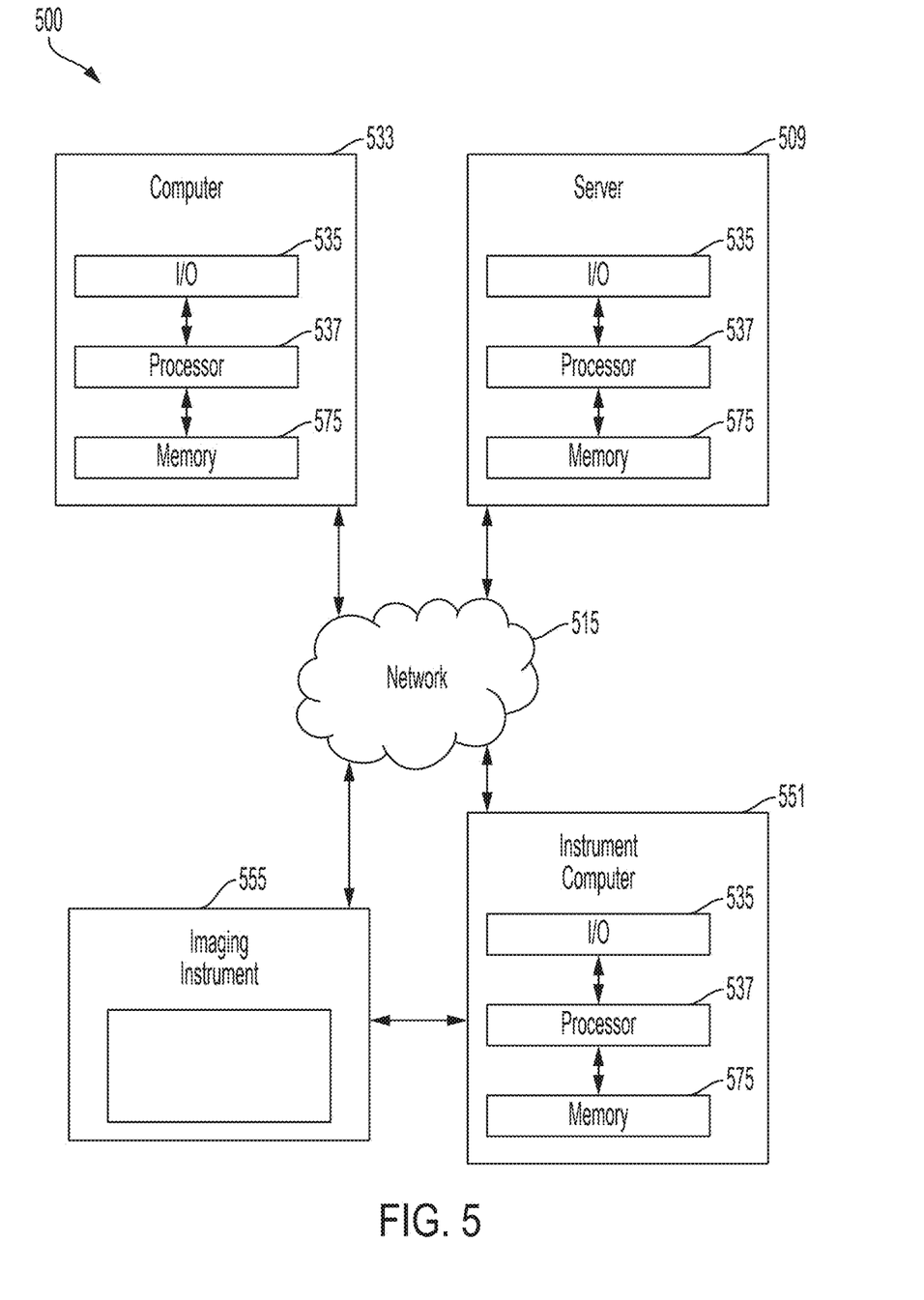
FIG. 5 shows a block diagram of a computer system on which various embodiments of the technology described herein may be practiced.

FIG. 5 shows a block diagram of a computer system 500 on which various embodiments of the technology described herein may be practiced. The system 500 includes at least one computer 533. Optionally, the system 500 may further include one or more of a server computer 509 and an imaging instrument 555 (e.g., one of the instruments described above), which may be coupled to an instrument computer 551. Each computer in the system 500 includes a processor 537 coupled to a tangible, non-transitory memory device 575 and at least one input/output device 535. Thus the system 500 includes at least one processor 537 coupled to a memory subsystem 575 (e.g., a memory device or collection of memory devices). The components (e.g., computer, server, instrument computer, and imaging instrument) may be in communication over a network 515 that may be wired or wireless and wherein the components may be remotely located or located in close proximity to each other. Using those components, the system 500 is operable to receive or obtain image data such as pathology images, histology images, or tissue images and annotation and score data as well as test sample images generated by the imaging instrument or otherwise obtained. In certain embodiments, the system uses the memory to store the received data as well as the model data which may be trained and otherwise operated by the processor.

In some embodiments, some or all of system 500 is implemented in a cloud-based architecture. The cloud-based architecture may offer on-demand access to a shared pool of configurable computing resources (e.g. processors, graphics processors, memory, disk storage, network bandwidth, and other suitable resources). A processor in the cloud-based architecture may be operable to receive or obtain training data such as pathology images, histology images, or tissue images and annotation and score data as well as test sample images generated by the imaging instrument or otherwise obtained. A memory in the cloud-based architecture may store the received data as well as the model data which may be trained and otherwise operated by the processor. In some embodiments, the cloud-based architecture may provide a graphics processor for training the model in a faster and more efficient manner compared to a conventional processor.

Processor refers to any device or system of devices that performs processing operations. A processor will generally include a chip, such as a single core or multi-core chip (e.g., 12 cores), to provide a central processing unit (CPU). In certain embodiments, a processor may be a graphics processing unit (GPU) such as an Nvidia Tesla K80 graphics card from NVIDIA Corporation (Santa Clara, CA). A processor may be provided by a chip from Intel or AMD. A processor may be any suitable processor such as the microprocessor sold under the trademark XEON E5-2620 v3 by Intel (Santa Clara, CA) or the microprocessor sold under the trademark OPTERON 6200 by AMD (Sunnyvale, CA). Computer systems may include multiple processors including CPUs and or GPUs that may perform different steps of the described methods. The memory subsystem 575 may contain one or any combination of memory devices. A memory device is a mechanical device that stores data or instructions in a machine-readable format. Memory may include one or more sets of instructions (e.g., software)

which, when executed by one or more of the processors of the disclosed computers can accomplish some or all of the methods or functions described herein. Each computer may include a non-transitory memory device such as a solid state drive, flash drive, disk drive, hard drive, subscriber identity module (SIM) card, secure digital card (SD card), micro SD card, or solid state drive (SSD), optical and magnetic media, others, or a combination thereof. Using the described components, the system 500 is operable to produce a report and provide the report to a user via an input/output device. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the systems and methods described herein. Accordingly, the foregoing description and drawings are by way of example only.

References and citations to other documents, such as patents, patent applications, patent publications, journals, books, papers, web contents, have been made throughout this disclosure and in any patent applications incorporated by reference herein. All such documents are hereby incorporated herein by reference in their entirety for all purposes.

What is claimed is:

1. A system for training a deep learning model to assess liver pathology, the system comprising:
    at least one computer hardware processor; and
    at least one non-transitory computer-readable storage medium storing processor-executable instructions that, when executed by the at least one computer hardware processor, cause the at least one computer hardware processor to perform:
        accessing a plurality of annotated liver pathology image associated with a group of patients in one or more randomized controlled clinical trials of nonalcoholic steatohepatitis therapy, wherein each of the plurality of annotated liver pathology images includes at least one annotation describing one or more tissue characteristic categories for a portion of the image;
        training the deep learning model based on the plurality of annotated liver pathology images to predict the one or more tissue characteristic categories for a liver pathology image, wherein the one or more tissue characteristic categories are selected from a group comprising steatosis, lobular inflammation, hepatocyte ballooning, and fibrosis stage;
        storing the trained deep learning model on at least one storage device; and
        for a liver pathology image, evaluating a performance of the deep learning model by comparing a fraction of tissue area in the liver pathology image assigned to each NAS component with an ordinal score determined by a pathologist, wherein the ordinal score is determined based on the NAS components, wherein intra-observer reproducibility of the ordinal score of the liver pathology image by multiple pathologists is lower than reproducibility of predictions from multiple iterations of the trained deep learning model processing the liver pathology image,
    wherein a group comprising steatosis, lobular inflammation, and hepatocyte ballooning corresponds to components of a nonalcoholic fatty liver disease activity score (NAS).

2. The system of claim 1, wherein the processor-executable instructions cause the at least one computer hardware processor to further perform:
    measuring a feature at or prior to the therapy of a patient, and measuring the feature at a time point following therapy of the patient and calculating differences in feature values to determine treatment-dependent effects.

3. The system of claim 1, wherein the processor-executable instructions cause the at least one computer hardware processor to further perform:
    processing, using the trained deep learning model, a liver pathology image to generate predicted one or more tissue characteristic categories for the liver pathology image; and
    generating, for the liver pathology image, based on the predicted one or more tissue characteristic categories, a slide-level continuous score that corresponds to an underlying heterogeneous pattern of fibrosis observed in the liver pathology image.

4. The system of claim 3, wherein the one or more tissue characteristic categories are predicted on a pixel-level basis.

5. The system of claim 3, wherein the slide-level continuous score represents a continuum of severity of cellular and stromal injury to capture disease heterogeneity among different patients, wherein an ordinal classification system does not capture the disease heterogeneity among the different patients.

6. The system of claim 1, wherein the processor-executable instructions cause the at least one computer hardware processor to further perform:
   extracting values for a plurality of complex features from each of the annotated liver pathology images, wherein the plurality of complex features includes one or more features not included in the NAS components; and
   training the deep learning model based on the plurality of annotated liver pathology images and the values for the plurality of complex features.

7. The system of claim 6, wherein the plurality of complex features comprises at least one ratio of the NAS components, including a ratio of area of hepatocellular ballooning to steatosis.

8. The system of claim 6, wherein the one or more features not included in the NAS components include portal inflammation and bile duct.

9. The system of claim 1, wherein the processor-executable instructions cause the at least one computer hardware processor to further perform:
   determining a score for a response metric that captures change in fibrosis pattern before and following the therapy by computing a distance between distribution of fibrosis stages at baseline and following the therapy.

10. The system of claim 9, wherein the processor-executable instructions cause the at least one computer hardware processor to further perform:
   based on a threshold, classifying patients as responder or non-responder to the therapy based on the score for the response metric for a respective patient.

11. The system of claim 1, wherein the deep learning model comprises one or more deep convolutional neural networks.

* * * * *